United States Patent [19]
Tsuchiya et al.

[11] Patent Number: 5,476,772
[45] Date of Patent: Dec. 19, 1995

[54] PRETREATMENT OF SAMPLE FOR ENDOTOXIN MEASUREMENT

[75] Inventors: Masakazu Tsuchiya; Kazuaki Harada, both of Amagasaki, Japan

[73] Assignee: Wako Pure Chemical Industries, Ltd., Osaka, Japan

[21] Appl. No.: 5,261

[22] Filed: Jan. 19, 1993

[30] Foreign Application Priority Data

Jan. 24, 1992 [JP] Japan ................... 4-034197

[51] Int. Cl.$^6$ ............... C12Q 1/37; C12Q 1/00
[52] U.S. Cl. ................ 435/23; 435/4; 435/18; 435/7.9; 435/25
[58] Field of Search .................. 435/23, 18, 4, 435/7.9, 25, 803, 7.32, 240.3; 514/8, 18

[56] References Cited

U.S. PATENT DOCUMENTS

| | | | |
|---|---|---|---|
| 4,221,865 | 9/1980 | Dubczak et al. | 435/4 |
| 4,221,866 | 9/1980 | Cotter | 435/4 |
| 4,276,050 | 6/1981 | Firca et al. | 435/18 |
| 4,495,294 | 1/1985 | Nakahara et al. | |
| 4,663,298 | 5/1987 | Urbascheck et al. | 436/502 |
| 5,019,502 | 5/1991 | Rienstra et al. | 435/803 |
| 5,151,266 | 9/1992 | Morgan, Jr. et al. | 514/8 |
| 5,389,547 | 2/1995 | Tanaka et al. | 435/4 |

FOREIGN PATENT DOCUMENTS 2080524  2/1982  United Kingdom.

OTHER PUBLICATIONS

Derwent Publications Ltd., London, GB; AN 92–070312 & JP-A-4 016 765 (Seikagaku Kogyo KK) 21 Jan. 1992 (Abstract).
Derwent Publications Ltd., London, GB; AN 90–213325 & JP-A-2 143 164 (Toray Ind Inc) 1 Jun. 1990 (Abstract).
Journal of Laboratory and Clinical Medicine; vol. 75, No. 6, Jun. 1970, St. Louis US pp. 903–911; J. Levine et al. 'Detection of endotoxin in human blood and demonstration of an inhibitor'.
Thrombosis Research, vol. 27; 51–57, 1982.
Journal of Biochemical and Biophysical Methods, vol. 18, 97–104, 1989.
Microbiol. Immunol., vol. 35 (4), 303–314, 1991.
The Lancet, vol. 1, 1272–1274, 1975.
H. Fukui et al., Record of 8th Endotoxin Clinical Study Meeting, Yo–do–sha, pp. 59–66, 1989.
Kambayashi et al, J. Biochem & Biophy Meth, vol. 18, pp. 97–104, 1989.

Primary Examiner—Michael G. Wityshyn
Assistant Examiner—Louise N. Leary
Attorney, Agent, or Firm—Armstrong, Westerman, Hattori, McLeland & Naughton

[57] ABSTRACT

A pretreating method for a sample such as plasma for endotoxin measurement which includes diluting the sample with a surfactant-containing aqueous solution, and subjecting the diluted sample to heat treatment can prevent influences of inhibitors, etc. present in the sample and gives high recovery of endotoxins.

10 Claims, 4 Drawing Sheets

PRETREATMENT OF SAMPLE FOR ENDOTOXIN MEASUREMENT

BACKGROUND OF THE INVENTION

This invention relates to a process for pretreating a sample for endotoxin measurement, and a pretreating solution used for such a process so as to prevent influences of inhibitors and/or substances showing false positives contained in the sample (hereinafter referred to as "inhibitors, etc.") in the measurement of endotoxin concentration in the sample.

Endotoxin concentration in a sample is measured by detecting an activity of an enzyme (protease, etc.) or the gelation reaction which is caused by the reaction between a horseshoe crab hemocyte lysate (hereinafter referred to as "AL solution") and endotoxins.

In such a measurement there is a fear of presence of inhibitors, etc. which influence the activation of enzymes (protease, etc.) and the gelation reaction.

Endotoxins are lipopolysaccharides (LPS) present mainly in cell walls of Gram-negative bacteria and are known as strong pyrogens. Therefore, it is important to detect endotoxins in medical devices and drugs for injection, and the like. The process for determining endotoxins is described in the Pharmacopoeia of Japan and the United States. Further, endotoxins are considered as a main cause of shock in Gram-negative bacterium infections. In clinical diagnosis, the endotoxin measurement in plasma is used for diagnosis of Gram-negative bacterium infections, judgement of therapeutic effects and recuperation of Gram-negative bacterium infections, early diagnosis of endotoxin shock, etc.

On the other hand, the AL solution has a property of being activated by endotoxins and causing activation of enzymes (protease, etc.) and the gelation reaction. By applying this property, simple and non-expensive endotoxin detection methods are widely used in the fields of medical science, pharmacology and microbiology. Examples of such methods are a method for calorimetrically measuring the degree of activation of enzymes (protease, etc.), a method of applying a gelation reaction, i.e. so-called Limulus test (hereinafter referred to as "Limulus test, etc."), etc.

But, in order to measure endotoxins in plasma, it is necessary to conduct pretreatment of the plasma to be tested by some method so as to prevent influences of the inhibitors, etc. contained in the plasma. Methods of pretreatment of plasma now employed for such a purpose are a perchloric acid treatment (H. Tamura et al: Thromb. Res., 27, 51–57, 1982, etc.), a new perchloric acid treatment (K. Inada et al: Microbiol. Immunol., vol. 35(4), 303–314, 1991, etc.), a dilution and heating treatment (M. S. Cooperstock et al: Lancet, 1, 1272, 1975), etc. But, these treatments have various problems therein and cannot be said as desirable treatments.

For example, the perchloric acid treatment comprises adding perchloric acid to plasma, heating at 37° C. for 20 minutes, removing a precipitate of denatured material by a centrifuge at 3000 r.p.m. for 15 minutes, neutralizing a supernatant with sodium hydroxide, and subjecting the thus treated plasma to the measurement. This treatment has various problems in that the procedures are complicated, a part of endotoxins is taken into the precipitate to lower the recovery of endotoxins, etc.

The new perchloric acid treatment comprises adding sodium hydroxide to plasma, heating at 37° C. for 5 minutes, heating at 37° C. for 10 minutes after addition of perchloric acid, dissolving a produced precipitate with sodium hydroxide, adding a Tris buffer solution to the resulting solution so as to adjust the pH, and subjecting the resulting solution to the measurement. This treatment has the same problem as the perchloric acid treatment in that the procedures are complicated.

The dilution and heating treatment comprises diluting plasma with distilled water 10 times, heating at 100° C. for 10 minutes, and subjecting the thus treated solution to the measurement. This treatment is advantageous in that the procedures are simple, but has a problem in that the recovery of endotoxin added to plasma is low very often.

Apart from the above-mentioned treatments, a treatment of addition of Tween 80 (a trade name of a surfactant mfd. by Kao Atlas Co., Ltd.) is reported recently (H. Fukui et al: Record of 8th Endotoxin Clinical Study Meeting, Yo-do-sha, 59–66, 1989). According to this treatment, plasma is diluted and heated, added with Tween 80 so as to make the final concentration 1% w/v, stirred for 5 minutes under ice cooling using a ultrasonic treating machine, and subjected to the measurement. This treatment also has problems in that the procedures are complicated considerably and a special device such as the ultrasonic treating machine is necessary, etc.

SUMMARY OF THE PRESENT INVENTION

It is an object of the present invention to provide a process for pretreating a sample (mainly plasma, serum, etc.) for the Limulus test, etc. overcoming problems mentioned above so as to make practical use possible with simple procedures and with good recovery of endotoxins.

It is another object of the present invention to provide a pretreating solution used for such a process.

The present invention provides a process for pretreating a sample for endotoxin measurement, which comprises diluting the sample with an aqueous solution containing a surfactant, and subjecting the diluted sample to heat treatment.

The present invention also provides a pretreating solution comprising a surfactant in an amount of 0.005 to 0.3% weight/volume (w/v), being free from endotoxins and having a property of not inhibiting nor enhancing the reaction between a horseshoe crab hemocyte lysate and endotoxins.

DESCRIPTION OF THE PREFERRED EMBODIMENTS

Figure 1:
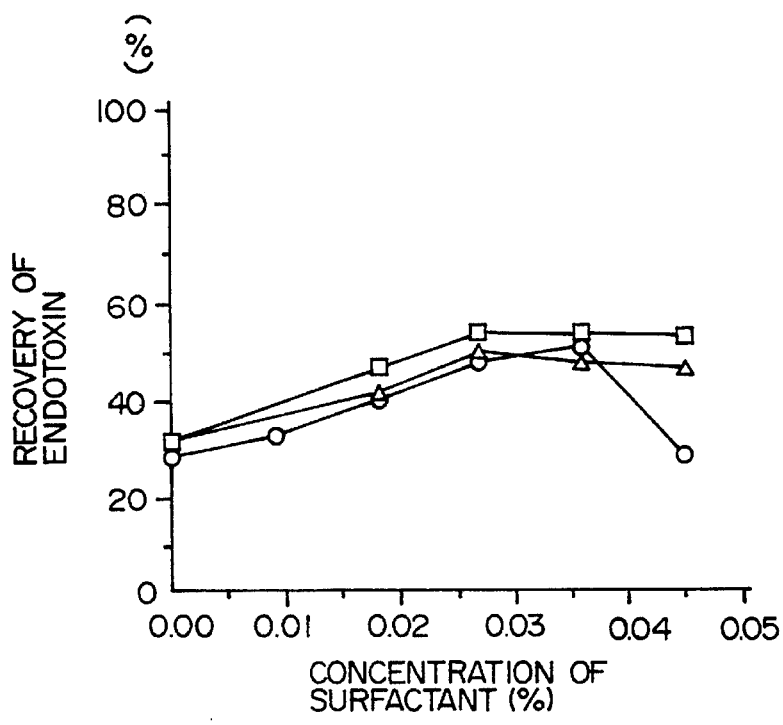
FIG. 1 is a graph showing the recovery of endotoxin in plasma in Example 1 of the present invention.

The pretreating process of the present invention can remove influences of the inhibitors, etc. present in the sample such as plasma, serum, etc. in the endotoxin measurement by the Limulus test, etc. Such a process is simple, can be used practically and good in the recovery of endotoxins. The pretreating process of the present invention comprises diluting the sample such as plasma with an aqueous solution containing surfactant, and subjecting the diluted sample to heat treatment. The recovery of endotoxins in the sample such as plasma is the same or more than that of the prior art processes. Further, even if there is used a sample wherein non-specific turbidity change takes place at the time of measurement in the case of diluting with only water for injection, followed by heating, no such non-specific turbidity change takes place in the process of the present invention.

As the surfactant, there can be used those having no property of inhibiting or enhancing the reaction between endotoxins and the AL solution after the pretreatment of the sample according to the present invention, and causing no non-specific turbidity change at such a reaction. There is no particular limitation thereto.

Examples of such surfactants are as follows.

Nonionic surfactants, for example, polyoxyethylene alkyl ethers such as polyoxyethylene cetyl ether, polyoxyethylene lauryl ether, etc.; polyoxyethylene alkyl phenyl ethers such as polyoxyethylene octyl phenyl ether, polyoxyethylene nonyl phenyl ether, etc.; polyoxyethylene alkyl esters such as polyoxyethylene sorbitan monooleate, polyoxyethylene sorbitan monopalmitate, polyoxyethylene sorbitan monostearate, polyoxyethylene sorbitan trioleate, etc.; methylglucamide derivatives such as octanoyl-N-methylglucamide, nonanoyl-N-methylglucamide, decanoyl-N-methylglucamide, etc.; and alkyl sugar derivatives such as n-octyl-µ-D-glucoside, etc.

Anionic surfactants, for example, sodium dodecylsulfate (SDS), laurylbenzenesulfonic acid, deoxycholic acid, cholic acid, tris(hydroxymethyl)aminomethane dodecylsulfate (Tris DS), etc.

Cationic surfactants, for example, alkylamine salts such as octadecylamine acetate, tetradecylamine acetate, stearylamine acetate, laurylamine acetate, lauryldiethanolamine acetate, etc.; quaternary ammonium salts such as octadecyltrimethylammonium chloride, dodecyltrimethylammonium chloride, cetyltrimethylammonium chloride, cetyltrimethylammonium bromide, allyltrimethylammonium methylsulfate, benzalkonium chloride, tetradecyldimethylammonium chloride, octadecyldimethylbenzylammonium chloride, lauryldimethylbenzylammonium chloride, etc.; and alkylpyridinium salts such as laurylpyridinium chloride, stearylamidomethylpyridinium chloride, etc.

Amphoteric surfactants, for example, 3-[(3-cholamidoamidopropyl)dimethylammonio]-2-hydroxy-1-propane sulfonate, 3-[(3-cholamidoamidopropyl)dimethylammonio]-2-hydroxy-1-propane sulfonate, etc.

Natural surfactants, for example, saponin (derived from soybean), digitonin, etc.

Among these surfactants, nonionic surfactants and amphoteric surfactants are preferable.

Further, these surfactants can be used singly or as a mixture thereof.

The concentration of surfactant used changes depending on the kind of surfactant and the sample to be treated, and is sufficient when the influences of inhibitors, etc. contained in the sample can be prevented. The concentration at the time of heat treatment is preferably 0.005 to 0.3% w/v, more preferably 0.01 to 0.2% w/v, and most preferably 0.01 to 0.1% w/v.

For practicing the present invention, the sample such as plasma is diluted with the aqueous solution containing a surfactant in a predetermined amount, and then, subjected to heat treatment.

The surfactant-containing aqueous solution can be prepared by adding a surfactant to distilled water to have a proper concentration, autoclaving at 121° C. for 20 minutes, and finally adjusting the concentration to usually 0.005 to 0.3% w/v, preferably 0.01 to 0.2% w/v, more preferably 0.01 to 0.1% w/v with endotoxin free water such as distilled water for injection. The surfactant-containing aqueous solution should be endotoxin free and preferably be admitted that it does not enhance or inhibit the reaction of Limulus test, etc. Needless to say, the concentration of the surfactant-containing aqueous solution can be adjusted before the autoclaving treatment.

The dilution rate of the sample with the surfactant-containing aqueous solution is not particularly limited. But in the case of using plasma, etc. as a sample, when the degree of dilution is too low, there arise various problems in that the viscosity of the diluted plasma solution increases by denaturation of plasma protein at the time of heating, precipitation takes place in the diluted plasma solution. On the other hand, when the degree of dilution is too high, there often bringing about a problem of not properly detecting endotoxins. Thus, the dilution is preferably 5 to 20 times, more preferably 8 to 12 times.

The temperature of heat treatment is preferably 60° to 100° C., more preferably about 70° to 90° C.

The heating time is preferably 3 to 20 minutes, more preferably about 5 to 15 minutes.

The thus pretreated sample solution is, then, subjected to the endotoxin measurement by a conventional method such as the so-called Limulus test, a conventional method using the AL solution, e.g. a kinetic turbidimetric technique using a special device such as Toxinometer ET-201 (mfd. by Wako Pure Chemical Industries, Ltd.), LAL-5000 (mfd. by Associates of Cape Cod Inc. (ACC)).

As the AL solution, there can be used those conventionally used for endotoxin measurement, for example, that prepared from freeze-dried products of AL solutions commercially available from ACC, Heamachem, Inc., Whittaker Bioproducts, Inc., Teikoku Hormon Mfg. Co., Ltd., Endosafe Inc., etc. It is also possible to use those hemocyte lysate of horseshoe crab belonging to Limulus genus, Tachypleus genus or Carcinoscorpins genus and being able to produce activation of enzymes (protease, etc.) and gelation reaction by the reaction with endotoxins.

The present invention is illustrated by way of the following Examples.

Example 1

(Reagents)

(i) Endotoxin Solution

A stock solution of 1 mg/ml was prepared by dissolving 10 mg of *E. Coli 0111*:B4 LPS (mfd. by Difco Co.) in 10 ml of water for injection. The stock solution was properly diluted with water for injection for practical use.

(ii) AL Solution

The AL solution was prepared by dissolving a freeze-dried product of AL solution derived from horseshoe crab of Limulus genus (hereinafter referred to as "LAL", sold by Wako Pure Chemical Industries, Ltd., 50-test vials labeled sensitivity of 0.03 Eu/ml in water for injection (LAL dissolved solution).

(iii) Surfactant-Containing Aqueous Solution

Polyoxyethyleneglycol p-t-octylphenyl ether (nonionic surfactant, mfd. by Wako Pure Chemical Industries, Ltd.) was diluted with water for injection to 20% w/v, followed by autoclaving at 121° C. for 20 minutes to give a stock solution. After diluting a part of the stock solution with water for injection properly, it was confirmed that the diluted stock solution was endotoxin free and did not enhance nor inhibit the Limulus test, etc.

(Procedures)

To each 750 µl of three kinds of normal human plasma, 15 µl of endotoxin solution having a predetermined concentration was added, respectively. The resulting endotoxin added plasma in an amount of 100 µl was diluted 10 times with 900 µl of water for injection or a surfactant-containing aqueous solution (concentration: 0.01 to 0.05% w/v), followed by heat treatment at 80° C. for 10 minutes (the final concentration of endotoxin: 9.8 pg/ml, the final concentration of surfactant: 0.009 to 0.045% w/v). After heat treatment, the diluted plasma was instantly cooled with ice. The endotoxin concentration in the diluted plasma was measured according to a conventional method using a Toxinometer ET-201 (mfd. by Wako Pure Chemical Industries, Ltd.) as follows.

After mixing 0.1 ml of the LAL solution with 0.1 ml of the above-mentioned diluted plasma with stirring, a time required for reducing the transmitted light amount through the resulting mixed solution by 5% (hereinafter referred to as "Tg") while maintaining at 37° C. was measured. The same measurement as mentioned above was conducted using endotoxin solutions as samples having various concentrations obtained by using water for injection and predetermined endotoxin solution. A calibration curve showing a relationship between the endotoxin concentration and Tg was prepared. Based on the calibration curve, the endotoxin concentration in a sample was calculated.

(Results)

The obtained results are shown in FIG. 1. FIG. 1 was obtained by plotting the endotoxin recovery (%) (ordinate axis) in the obtained dilution treated plasma against the concentration of surfactant (abscissa axis) at the time of heat treatment and lined. In FIG. 1, -o- shows the results obtained by using the endotoxin added plasma 1, -Δ- shows the results obtained by using the endotoxin added plasma 2, and -□- shows the results obtained by using the endotoxin added plasma 3.

As is clear from the results of FIG. 1, the recovery in the case of using water for injection is about 30%, whereas the recovery increases to about 50% by using about 0.03 to 0.04% w/v surfactant-containing aqueous solution (the surfactant concentration at the time of heat treatment: about 0.027 to 0.036% w/v). Thus, the recovery of endotoxin in plasma can be increased by the process of the present invention.

The same results as mentioned above were also obtained when Anphitol 20N (a trade name of amphoteric surfactant, mfd. by Kao Corp., lauryldimethylamine oxide) was used in place of polyoxyethyleneglycol p-t-octylphenyl ether.

Example 2

(Reagents)

(i) AL Solution

The same as that used in Example 1.

(ii) Endotoxin Solution

The same as that used in Example 1.

(iii) Surfactant-Containing Aqueous Solution

Polyoxyethylene monooleate (nonionic surfactant, mfd. by Wako Pure Chemical Industries, Ltd.) was diluted with water for injection to 20% w/v, followed by autoclaving at 121° C. for 20 minutes to give a stock solution. After diluting a part of the stock solution with water for injection properly, it was confirmed that the diluted stock solution was endotoxin free and did not enhance nor inhibit the Limulus test, etc.

(Procedures)

To each 1.1 ml of three kinds of normal human plasma, 11 µl of endotoxin solution having a predetermined concentration was added, respectively. The resulting endotoxin added plasma in an amount of 100 µl was diluted 10 times with 900 µl of water for injection, or a surfactant-containing aqueous solution (concentration: 0.002 to 0.2% w/v), followed by heat treatment at 80° C. for 10 minutes (the final concentration of endotoxin: 10 pg/ml, the final concentration of surfactant: 0.018 to 0.18% w/v). After heat treatment, the diluted plasma was instantly ice cooled. The endotoxin concentration in the diluted plasma was measured in the same manner as described in Example 1.

(Results)

Figure 2:
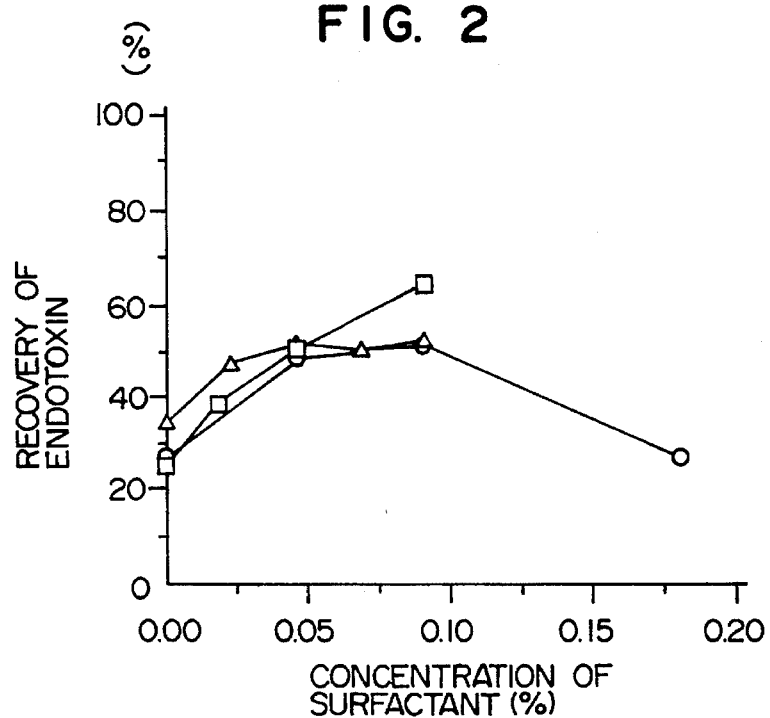
FIG. 2 is a graph showing the recovery of endotoxin in plasma in Example 2 of the present invention.
Figure 3A:
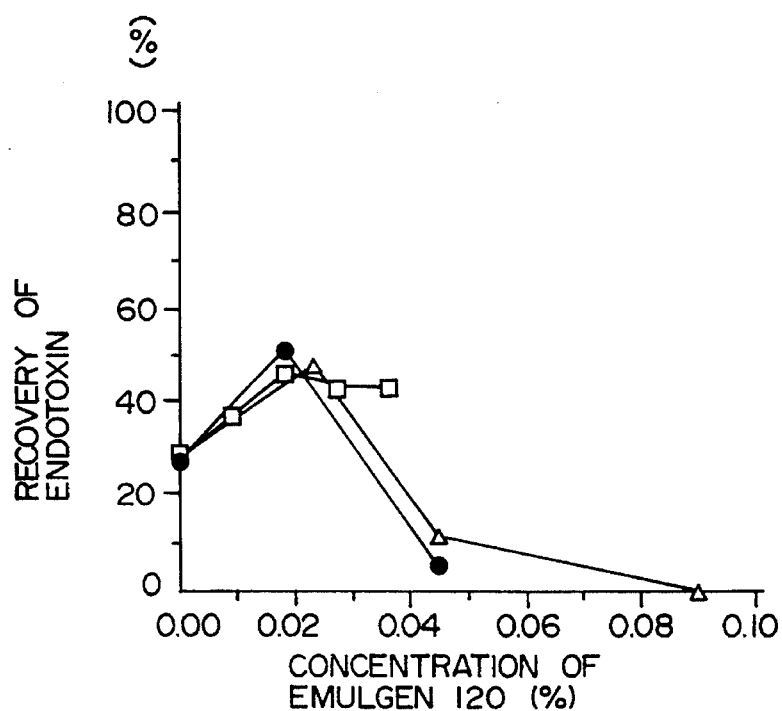
FIGS. 3(a) to 3(d) are graphs showing the recovery of endotoxin in Example 3 of the present invention.
Figure 3B:
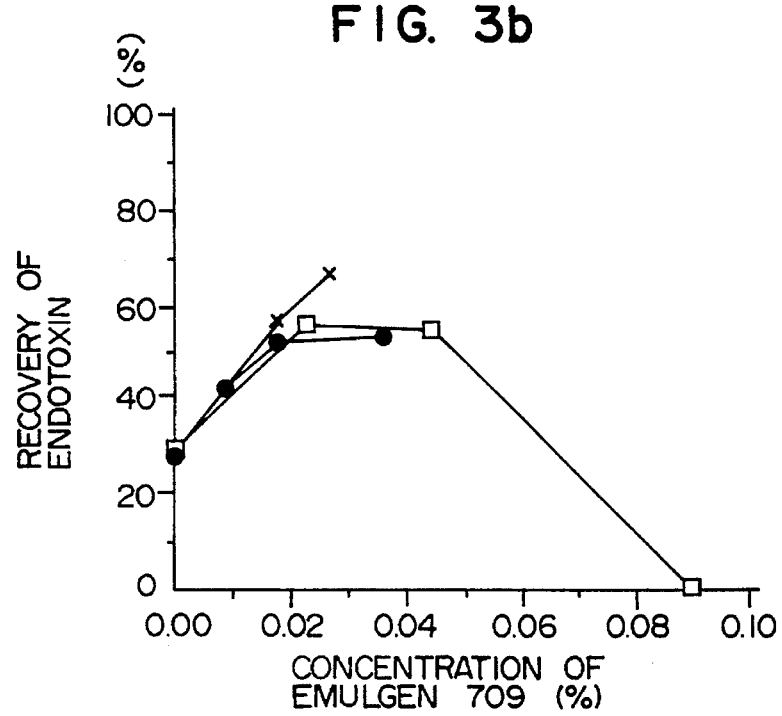
Figure 3C:
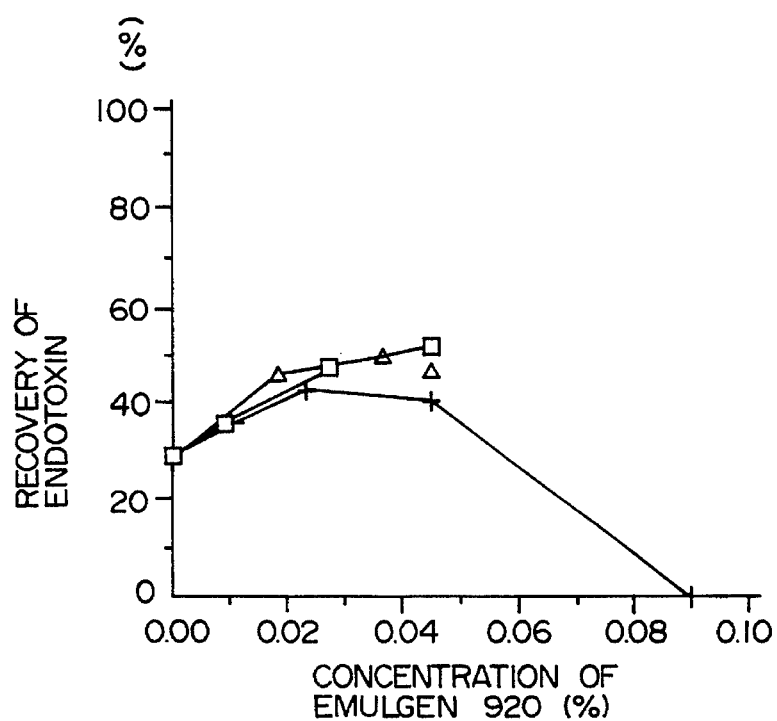
Figure 3D:
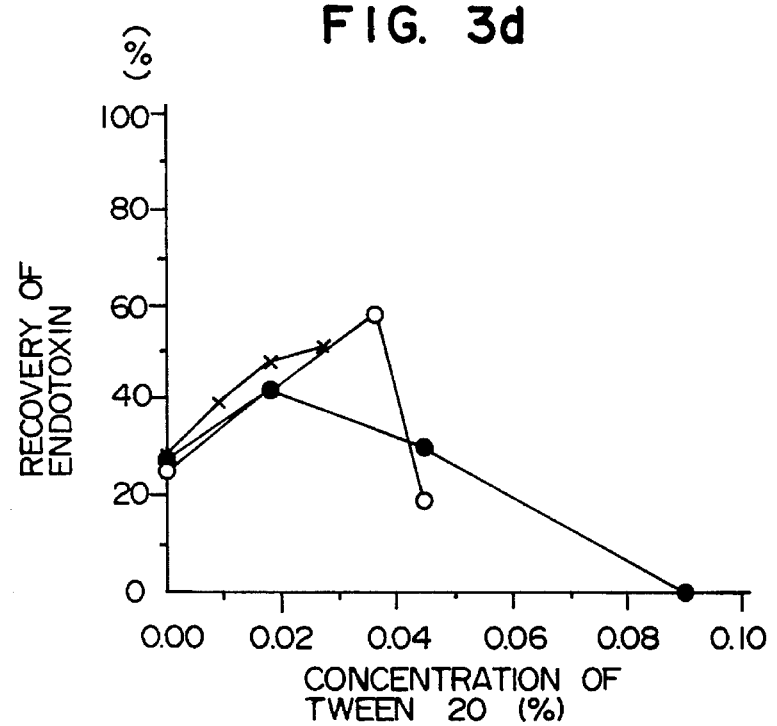

The obtained results are shown in FIG. 2. FIG. 2 was obtained by plotting the endotoxin recovery (%) (ordinate axis) in the obtained dilution treated plasma against the concentration of surfactant (abscissa axis) at the time of heat treatment and lined. In FIG. 2, -o- shows the results obtained by using the endotoxin added plasma 1, -Δ- shows the results obtained by using the endotoxin added plasma 2, and -□- shows the results obtained by the endotoxin added plasma 3.

As is clear from the results of FIG. 2, the recovery in the case of using water for injection is about 30%, whereas the recovery increases to 50% or higher by using about 0.05 to 0.1% w/v surfactant-containing aqueous solution (the surfactant concentration at the time of heat treatment: about 0.045 to 0.09% w/v). Thus, the recovery of endotoxin in plasma can be increased by the process of the present invention.

Example 3

(Reagents)

(i) AL Solution

The same as that used in Example 1.

(ii) Endotoxin Solution

The same as that used in Example 1.

(iii) Surfactant-Containing Aqueous Solution

Surfactant-containing aqueous solutions were prepared in the same manner as described in Example 1 except for using as a surfactant Emulgen 120 (polyoxyethylene lauryl ether), Emulgen 709 (polyoxyethylene higher alcohol ether), Emulgen 920 (polyoxyethylene nonylphenyl ether) (these being nonionic surfactants, trade names, mfd. by Kao Corp.) and Tween 20 (polyoxyethylene sorbitan monolaurate) (nonionic surfactant, a trade name, mfd. by Kao Corp.).

(Procedures)

To each 1.1 ml of six kinds of normal human plasma, 11 μl of endotoxin solution having a predetermined concentration was added, respectively. The resulting endotoxin added plasma in an amount of 100 μl was diluted 10 times with 900 μl of water for injection or a surfactant-containing aqueous solution (concentration: 0.0125 to 0.1% w/v), followed by heat treatment at 80° C. for 10 minutes (the final concentration of endotoxin: 10 pg/ml, the final concentration of surfactants: 0.01125 to 0.09% w/v). After heat treatment, the diluted plasma was instantly ice cooled. The endotoxin concentration in the diluted plasma was measured in the same manner as described in Example 1.

(Results)

The obtained results are shown in FIGS. 3(a) to 3(d). FIGS. 3(a) to 3(d) were obtained by plotting the endotoxin recovery (%) (ordinate axis) in the obtained dilution treated plasma against the concentration of surfactant (abscissa axis) at the time of heat treatment and lined. In FIGS. 3(a) to 3(d), -o- shows the results obtained by using the endotoxin added plasma 1, -●- shows the results obtained by using the endotoxin added plasma 2, -□- shows the results obtained by using the endotoxin added plasma 3, -+- shows the results obtained by using the endotoxin added plasma 4, -Δ- shows the results obtained by using the endotoxin added plasma 5, and -×- shows the results obtained by using the endotoxin added plasma 6.

As is clear from the results shown in FIGS. 3(a) to 3(d), the recovery in the case of using water for injection is about 30%, whereas the recovery of endotoxin in plasma increases to 50% or higher depending on concentrations by using the surfactant-containing aqueous solutions of the present invention. Particularly when the concentration of Emulgen 709 at the time of heat treatment is 0.027% w/v, the recovery becomes about 70%.

Example 4

(Reagents)

The same AL solution and endotoxin solution as used in Example 1 were used. Further, as the surfactant-containing aqueous solution, that prepared by using Emulgen 709 in Example 3 was used.

(Procedures)

To each 1.2 ml of five kinds of normal human plasma (A to E), 12 μl of endotoxin solution having a predetermined concentration was added, respectively. The resulting endotoxin added plasma in an amount of 100 μl was diluted 10 times with 900 μl of aqueous solution containing 0.03% w/v of Emulgen 709, followed by heat treatment at 80° C. for 5 minutes (the final concentration of endotoxin: 5.0 pg/ml, the final concentration of Emulgen 709 aqueous solution: 0.027% w/v). After heat treatment, the diluted plasma was instantly ice cooled. The endotoxin concentration in the diluted plasma was measured in the same manner as described in Example 1.

(Results)

Figure 4:
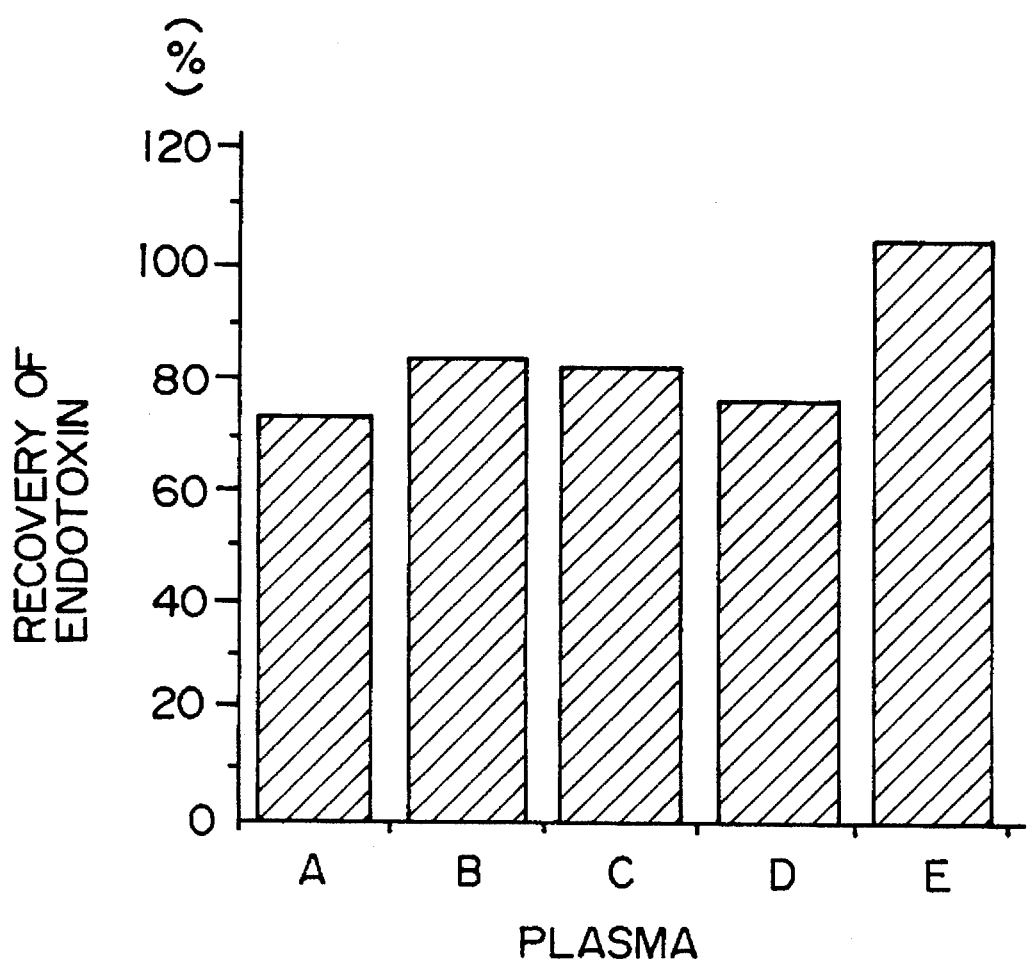
FIG. 4 is a graph showing the recovery of endotoxin in Example 4 of the present invention.

The obtained results are shown in FIG. 4. In FIG. 4, the endotoxin recovery (%) is plotted along the ordinate axis when the predetermined endotoxin added plasma is subjected to the dilution and heating treatment.

As is clear from the results of FIG. 4, the recovery in the case of using water for injection is about 30%, whereas the recovery increases to 70% or higher by using the surfactant-containing aqueous solutions of the present invention. Thus, the recovery of endotoxin in plasma can be increased by the process of the present invention.

Experiment 1

Comparison was made as to the endotoxin recovery when plasma was treated by prior art plasma pretreating method and by the pretreating method of the present invention.

(Reagents)

(i) Reagents for the Kinetic Turbidimetric Technique

The same AL solution and endotoxin solution as used in Example 1 were used.

(ii) Chromogenic Technique

Commercially available Endotoxin test-D kit (mfd. by Seikagaku Corp.) was used, provided that the same endotoxin solution as used in the kinetic turbidimetric technique mentioned above was used in place of that attached to the kit.

(iii) Surfactant-Containing Aqueous Solution

The same one as prepared in Example 3 using Emulgen 709 as a surfactant was used.

(iv) Perchloric Acid Solution

That having a concentration of 0.32M and endotoxin free was used.

(v) Sodium Hydroxide Solution

That having a concentration of 0.18M and endotoxin free was used.

(vi) Tris Buffer Solution

Endotoxin free 0.2M Tris(hydroxymethyl)aminomethane-HCl buffer solution (pH 8.0) was used.

(vii) Endotoxin Added Plasma

To 1 ml of normal human plasma 1, 10 μl of endotoxin solution (5 ng/ml) was added and mixed to give an endotoxin added plasma 1 having an endotoxin concentration of 50 pg/ml. Further, to 1 ml of normal human plasma 2, 10 μl of endotoxin solution (10 ng/ml) was added and mixed to give an endotoxin added plasma 2.

(Pretreatment of Plasma)

(i) Dilution and Heat Treatment

After mixing 100 μl of an endotoxin added plasma with 90 μl of water for injection, the heat treatment was conducted at 100° C. for 10 minutes, followed by instant ice cooling to give a sample of the dilution and heat treatment.

(ii) New Perchloric Acid Treatment

After mixing 100 μl of an endotoxin added plasma with 100 μl of sodium hydroxide solution, the heat treatment at 37° C. for 5 minutes was conducted. Then, 100 μl of perchloric acid solution was mixed with the resulting solution, followed by heat treatment at 37° C. for 10 minutes. Then, 200 μl of sodium hydroxide solution and 500 μl of Tris buffer solution were added to the resulting solution and mixed to give a sample of the new perchloric acid treatment.

(iii) Perchloric Acid Treatment

After mixing 300 μl of an endotoxin added plasma with 600 μl of perchloric acid solution, the heat treatment was conducted at 37° C. for 20 minutes, followed by centrifugal separation at 3000 r.p.m. for 15 minutes. The obtained supernatant in an amount of 400 μl was mixed with 400 μl of sodium hydroxide solution to give a sample of the perchloric acid treatment.

(iv) The Process of the Present Invention

Using the same reagents as used in Example 4 except for using the above-mentioned endotoxin added plasma, and treated in the same manner as described in Example 4, a sample of the present invention was given.

(Measurement of Endotoxin Recovery in Samples)

(i) Kinetic Turbidimetric Technique

The endotoxin concentration in the samples prepared by the above-mentioned 4 pretreating methods were measured using a Toxinometer ET-201 (mfd. by Wako Pure Chemical Industries, Ltd.). The measurement procedures were the same as in Example 1.

(ii) Chromogenic Technique

The endoxin concentrations in the samples prepared by the above-mentioned 4 pretreating methods were determined using an Endotoxin Test-D kit (kfd. by Seikagaku Corp.). The measuring procedures were conducted according to the manual for measuring procedures attached to the kit.

(Results)

The results are shown in Table 1.

TABLE 1

| Pretreating method | Measuring method | Endotoxin added plasma | Recovering (%) |
|---|---|---|---|
| Dilution & heat treatment | Kinetic turbidimetric technique | 1 | 26 |
| | | 2 | 19 |
| New perchloric acid treatment | | 1 | 28 |
| | | 2 | 20 |
| Perchloric acid treatment | | 1 | 3 |
| | | 2 | 1 |
| The process of present invention | | 1 | 75 |
| | | 2 | 70 |
| Dilution & heat treatment | Chromogenic technique | 1 | 24 |
| | | 2 | 26 |
| New perchloric acid treatment | | 1 | 34 |
| | | 2 | 28 |
| Perchloric acid treatment | | 1 | 5 |
| | | 2 | 2 |

TABLE 1-continued

| Pretreating method | Measuring method | Endotoxin added plasma | Recovering (%) |
|---|---|---|---|
| The process of present invention | | 1 | 90 |
| | | 2 | 85 |

As is clear from the results of Table 1, the best endotoxin recovery (%) is obtained by the pretreating method of the present invention either by the kinetic turbidimetric technique or the chromogenic technique.

As mentioned above, the present invention provides a simple method for pretreating a sample such as plasma for endotoxin measurement. Further, according to the process of the present invention, the endotoxin in the sample such as plasma can be detected with better recovery than prior art methods.

What is claimed is:

1. A process for pretreating a sample for endotoxin measurement, which consists essentially of diluting the sample with an aqueous solution containing a surfactant, said aqueous solution being endotoxin free and having a property of not inhibiting nor enhancing the reaction between a horseshoe crab hemocyte lysate and endotoxins, and heating the diluted sample at 60° to 100° C., whereby false positives in a subsequent endotoxin measurement are prevented and endotoxin recovery of 50% or more is provided in the subsequent endotoxin measurement.

2. A process according to claim 1, wherein the sample is plasma or serum.

3. A process according to claim 1, wherein the surfactant is contained in a concentration of 0.005 to 0.3% by weight/volume at the time of heat treatment.

4. A process according to claim 1, wherein the surfactant is a nonionic surfactant or an amphoteric surfactant.

5. A process according to claim 1, wherein the sample is diluted 5 to 20 times with an aqueous solution containing a surfactant.

6. A process according to claim 1, wherein the heat treatment is conducted for 3 to 20 minutes.

7. A process according to claim 1, wherein the heat treatment is conducted at 70° to 90° C.

8. A process according to claim 1, wherein the heat treatment is conducted at 70° to 90° C. for 3 to 20 minutes.

9. A process for measuring the concentration of endotoxin in a sample with a recovery of 50% or more and without false positives, which comprises subjecting the sample prior to measuring the concentration of the endotoxin to a pretreatment consisting essentially of diluting the sample with an aqueous solution containing a surfactant, said aqueous solution being endotoxin free and having a property of not inhibiting nor enhancing the reaction between a horseshoe crab hemocyte lysate and endotoxins, heating the diluted sample at 60° to 100° C., and to measuring the concentration of the endotoxin.

10. A process according to claim 9, wherein the endotoxin is measured by a Limulus test, a kinetic turbidimetric technique or a chromogenic technique.

* * * * *